United States Patent [19]
Bower et al.

[11] Patent Number: 5,503,704
[45] Date of Patent: Apr. 2, 1996

[54] NITROGEN BASED LOW TEMPERATURE DIRECT BONDING

[75] Inventors: Robert W. Bower, Davis; Mohd S. Ismail; Brian E. Roberds, both of West Sacramento, all of Calif.

[73] Assignee: The Regents of the University of California, Oakland, Calif.

[21] Appl. No.: 255,829

[22] Filed: Jun. 8, 1994

Related U.S. Application Data

[63] Continuation of Ser. No. 1,546, Jan. 6, 1993, abandoned.

[51] Int. Cl.$^6$ ...................................................... B32B 31/00
[52] U.S. Cl. .................. 156/281; 156/272.6; 156/308.6; 156/309.3; 156/629.1; 204/164; 216/34; 264/346; 427/399; 428/420
[58] Field of Search ............................ 156/272.6, 308.6, 156/309.3, 281, 629, 629.1; 264/346; 427/399; 204/164; 428/420; 216/34

[56] References Cited

U.S. PATENT DOCUMENTS

| | | | |
|---|---|---|---|
| 3,409,198 | 11/1968 | Peterman | 156/281 |
| 3,477,902 | 11/1969 | Tomasino et al. | 156/272.6 |
| 3,579,395 | 5/1971 | Rath | 156/272.6 |
| 5,215,636 | 6/1993 | Dankychev et al. | 204/164 |

FOREIGN PATENT DOCUMENTS

| | | | |
|---|---|---|---|
| 366208 | 5/1990 | European Pat. Off. | 156/281 |
| 60-46976 | 3/1985 | Japan | 156/629 |
| 2053026 | 2/1981 | United Kingdom | 204/164 |

OTHER PUBLICATIONS

J. B. Lasky; "Wafer Bonding For Silicon–On–Insulator Techniques"; Jan. 6, 1986; Appl. Phys. Lett. 48 (1).
Peterson, K. et al.; "Silicon Fusion Bonding For Pressure Sensors"; Jun. 1988; Solid State Sensor and Activator Workshop Technical Digest, Hilton Head Island, South Carolina.
Chung, G. S. et al.; "High Resolution Pressure Sensors Fabricated By Silicon Wafer Direct Bonding"; Jun. 6, 1991; Electronics Letters vol. 27, No. 12.
Bower, R. W. et al; "Aligned Wafer Bonding: A Key to Three Dimensional Microstrucures"; May 13, 1991; Journal of Electronics Materials vol. 20, No. 5.
Bower, Robert W. et al; "Design Consideration of a Digital Pressure Sensor Array"; Jun. 24, 1991; Transducers '91–International Conference on Solid State Sensors and Actuators, San Francisco, CA.
Ismail, M. S. et al.; "Digital Pressure–Switch Array with Aligned Silicon Fusion Bonding"; Nov. 1991; J. Micromech. Microeng. 1.
Yamada, A. et al.; "Bonding Silicon Wafer to Silicon Nitride With Spin–On Glass as Adhesive"; Mar. 26, 1987; Electronics Letters, vol. 23, No. 7.
Ismail, M. S. et al.; "Silicon Nitride Direct Bonding"; Jul. 5, 1990; Electronics Letters, Vo. 26, No. 14.
Harendt, C. et al.; "Silicon Direct Bonding for Sensor Applications: Characterization of the Bond Quality"; 1991; Sensors and Actuators A, 25–27.
Yasumoto, H. et al.; "Promising New Fabrication Process Developed For Stacked LSI's"; Dec. 1984; Technical Digest in IEEE Int. Electron Devices Mtg; San Francisco, CA.
Lodge, Kevin J. et al.; "The Impact of Packaging on the Reliability of Flip–Chip Solder Bonded Devices"; Dec. 1990; IEEE Transactions on Components, Hybrids, and Manufacturing Technology. vol. 13, No. 4.
Bengtsson, S.; "Semiconductor Wafer Bonding: A Review of Interfacial Properties and Applications"; Aug. 1992; Journal of Electronic Materials.
Ismail, M. S. et al; "Polysilicon and Titanium Disilicide––Polycide Fusion Bonding for 3–D Microdevices Applications; Technical Digest, Solid State Sensor and Actuator Workshop", Hilton Head Island, S.C., Jun. 1992.
Meuris, M. et al; "Investigating Techniques To Improve Gate–Oxide Integrity"; May 1992; Microcontamination.
Xu, X.–L. et al.; "Novel Two Step SDB Technology For High–Performance Thin–Film SOI/MOSFET Applications"; Mar. 1989; Electronic Letters, vol. 25, No. 6.
Farrens, S. N. et al.; "Mechanical Testing of Bonded Silicon on Insulator Wafers"; Proceedings of the Materials Research Society, 239B, Materials Research Society Meeting, Boston, MA, Dec. 1991.
Stengl, R. et al.; "A Model for the Silicon Wafer Bonding Process"; Oct. 1989; Jpn. J. Appl. Phys. vol. 28, No. 10.
Lee, R. W. et al.; "Diffusion of Hydrogen and Deuterium in Fused Quartz"; Feb. 15, 1962; The Journal of Chemical Physics, vol. 36, No. 4.
Liau, Z. L. et al.; "Wafer Fusion: A Novel Technique for Optoelectronic Device Fabrication and Monolithic Integration"; Feb. 19, 1990; Appl. Phys. Lett.; vol. 56, No. 8.
Ismail, M. S. et al.; "Platinum Silicide Fusion Bonding"; Jun. 20, 1991; Electronic Letters, vol. 27, No. 13.
Ismail, M. S. et al.; "Technological Consideration of Three Dimensional CMOS Devices Formed with Aligned Wafer Bonding"; proceedings of the First International Symposium on Semiconductor Wafer Bonding Science, Technology and Applications, Electrochemical Society Meeting, Phoenix, AZ, Oct. 13–17, 1991, p. 474.
Tong, Q.–Y. et al.; "Diffusion and Oxide Viscous Flow Mechanism in SDB Process and Silicon Wafer Rapid Thermal Bonding"; May 24, 1990; Electronics Letters, vol. 26, No. 11.
Xu, X–L et al.; "Silicon On Quartz By Solid State Diffusion Bonding (SSDB) Technology"; May 1988 Electronics Letters, vol. 24, No. 11.

*Primary Examiner*—John J. Gallagher
*Attorney, Agent, or Firm*—John P. O'Banion

[57] ABSTRACT

A process for direct bonding similar or dissimilar materials at low temperatures in which a material surface is rendered hydrophilic and reactive by creating nitrogen based radicals on the surface, the surface is direct bonded to a second surface, and the bonded surfaces are annealed at a temperature below approximately 500° C. A nitrogen based constituent is combined with an activator to render the surface hydrophilic and reactive through ammonia plasma activation or activation by use of hydrofluoric acid.

13 Claims, 4 Drawing Sheets

FIG. —3

NITROGEN BASED LOW TEMPERATURE DIRECT BONDING

CROSS-REFERENCE TO RELATED APPLICATIONS

This application is a continuation of application Ser. No. 08/001,546 filed on Jan. 6, 1993, now abandoned.

BACKGROUND OF THE INVENTION

1. Field of the Invention

This invention pertains generally to semiconductor direct bonding techniques, and more particularly to a process for establishing permanent bonds at low temperatures by using nitrogen as a bonding agent.

2. Description of the Background Art

Direct (fusion) bonding between layers of silicon and $SiO_2$ is a known alternative to using organic or inorganic bonding agents. However, in order to achieve a bond of satisfactory strength, the materials must be annealed at temperatures generally greater than 700° C. As a result, direct bonding techniques have been limited to applications wherein the materials to be bonded can withstand a high temperature anneal.

To expand the versatility of direct bonding, nitride layers have been considered as intermediate bonding agents. The effectiveness of using one such nitride layer, $Si_3N_4$, has been debated and even dismissed by those skilled in the art. For example, Lasky's article entitled "Wafer Bonding for Silicon-on-insulator Technologies" and published in Applied Physics Letters in January 1986, reported that $Si_3N_4$ was not a bondable surface. A similar conclusion was reached by Yamada, Kawasaki, and Kawashima in their article entitled "Bonding Silicon Wafer to Silicon Nitride with Spin-on Glass as Adhesive" and published in Electronic Letters in 1987. On the other hand, Bower, Ismail, Veteran and Marsh reported in an article entitled "Silicon Nitride Direct Bonding" and published in Electronic Letters in July 1990, that an oxidized surface of nitride could be bonded at high temperatures consistent with silicon fusion bonding. Furthermore, Harendt, Hofflinger, Graf and Penteker in their article entitled "Silicon Direct Bonding for Sensor Applications: Characterization of the Bond Quality" and published in Sensors and Actuators in 1991, reported that LPCVD $Si_3N_4$ could be direct bonded at temperatures greater than 800° C.

While conventional direct bonding is effective with a high temperature anneal, some materials are unable to withstand such high temperatures. Therefore, high temperature bonding is limited in its application. In addition, problems occur with thermal mismatching in bonded dissimilar materials. Therefore, a need exists for a process whereby direct bonding can be effected using a low temperature anneal.

None of the reported bonding techniques, however, provide for satisfactory bonding of $Si_3N_4$ or other nitride layers such TiN at low temperatures; that is, at temperatures below approximately 500° C. Quite remarkably, however, we have overcome the deficiencies in the prior art and opened the door to low temperature direct bonding by developing a process which utilizes a nitrogen based constituent and an activator to render material surfaces hydrophilic and reactive prior to bonding. Not only can we bond nitride surfaces, but any surface which is reactive with nitrogen. As a result, a low temperature anneal can be used to effectuate a strong bond.

The foregoing publications reflect the state of the art of which the applicant is aware and are tendered with the view toward discharging applicant's acknowledged duty of candor in disclosing information which may be pertinent in the examination of this application. It is respectfully stipulated, however, that none of these publications teach or render obvious, singly or when considered in combination, applicant's claimed invention.

SUMMARY OF THE INVENTION

The present invention generally comprises combining a nitrogen based constituent with an activator to render a surface both hydrophilic and reactive at low temperatures. By way of example and not of limitation, pure silicon or titanium can be rendered hydrophilic and reactive by subjecting the material to a plasma of $NH_3$. Furthermore, a nitride layer deposited on a substrate of Si, Ti, $SiO_2$, GaAs, InP or the like can be rendered hydrophilic and reactive either by subjecting it to a plasma of $NH_3$ or dipping it in a solution of dilute HF. Once the materials are rendered hydrophilic and reactive in this manner, the materials can be brought into physical contact at room temperature to form an initial bond, and thereafter annealed at a temperature below approximately 500° C. and typically within the range of approximately 90° C. to 300° C.

In general terms, the present invention can be represented by the relationship

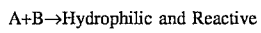

where:

A is a material surface to be bonded,

B is a surface activator, and

A or B includes nitrogen which we have discovered will render a surface both hydrophilic and reactive for low temperature direct bonding by creating nitrogen based radicals on the surface. The use of an $NH_3$ plasma or a solution of dilute HF as described in the examples above, represents the preferred chemistry in practicing the present invention. Where dilute HF is used in combination with a nitrogen based constituent, the material is preferably dipped in a solution of dilute hydrofluoric acid (approximately 1% HF) for approximately 10 seconds. Where a plasma of $NH_3$ is used in combination with either a nitrogen based constituent or a non-nitrogen based constituent, the material is preferably subjected to the plasma for at least 5 minutes in a deposition chamber. Once the material is rendered hydrophilic and reactive, the material is then direct bonded at room temperature and subsequently annealed at a temperature which is typically less than 500° C.

The present invention is particularly advantageous for fabrication of microstructures with materials which can withstand anneal temperatures of approximately 90° C. to 300° C. While the present invention can be used with anneal temperatures up to approximately 800° C., its advantages are best exhibited with anneal temperatures below approximately 500° C. since above that temperature silicon direct bonding can be employed using oxide as the bonding agent. Examples of applications which are possible with the present invention include a variety of optoelectronic and high frequency devices requiring use of materials such as GaAs and InP which cannot withstand high temperatures. In addition, low temperature bonding reduces the problems of thermal mismatch in bonding dissimilar materials. Therefore, materials such as GaAs and InP can be bonded to silicon to combine the power and economy of silicon integrated circuits with these high performance optoelectronic materials, or diamond or diamond-like carbon (dlc) heat sinks can be bonded to these materials to improve heat dissipation or mechanical durability. Furthermore, combinations of III-V and II-VI materials or devices that are otherwise difficult to merge with conventional heteroepitaxial techniques may be combined with low temperature bonding.

Additionally, the present invention can be applied to planarized surfaces of "completed" integrated circuit chips and wafers which include conventional A1 metalization. Normally, the A1 metalization would limit bonding procedures to those which use anneal temperatures not exceeding the range of approximately 400° C. to 450° C., thereby precluding conventional high temperature bonding. Therefore, organic glues and indium bumps have been used, both of which have limitations compared with clean, low temperature, nitride bonding.

Furthermore, the companion electrically conducting material in TiN complements $Si_3N_4$ to provide both insulating and conducting surfaces which can be bonded at low temperatures. TiN coated silicon wafers can be satisfactorily bonded at temperatures as low as 90° C. The combination of bonded TiN and $Si_3N_4$ surfaces would provide electrical, insulating and optical connections to be made between the joined layers for three dimensional optoelectronic elements.

Application of the present invention can be seen as far reaching. In essence, any material can be bonded in this manner so long as the material itself will react with a nitrogen donor, the material includes a nitride surface layer, the material contains a layer of another material which will react with a nitrogen donor, or the material contains a layer of another material which contains a nitride surface layer. For example, while GaAs does not contain a nitride surface layer and will not react with a nitrogen donor, the present invention can be employed by first depositing a layer of $Si_3N_4$ on the GaAs. In other words, any combination of a substrate material, nitrogen, and a suitable activator will produce a surface which is hydrophilic and reactive in accordance with the present invention by creating nitrogen-based radicals on the surface of the material.

An object of the invention is to provide for nitrogen based low temperature direct bonding.

Another object of the invention is to provide for direct bonding of similar or dissimilar materials.

Another object of the invention is to provide for integration of electronic circuity into microsensors.

Another object of the invention is to provide for integration of electronic circuity into optoelectronic devices.

Another object of the invention is to provide for iterative fabrication of multilayered devices.

Another object of the invention is to provide for direct bonding of semiconductor chips.

Another object of the invention is to initially bond materials at room temperature and anneal the bonds at low temperatures.

Another object of the invention is to provide for nitrogen to be used as a bonding agent between materials.

Another object of the invention is to provide for direct bonding at temperatures of approximately 300° C. or lower.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
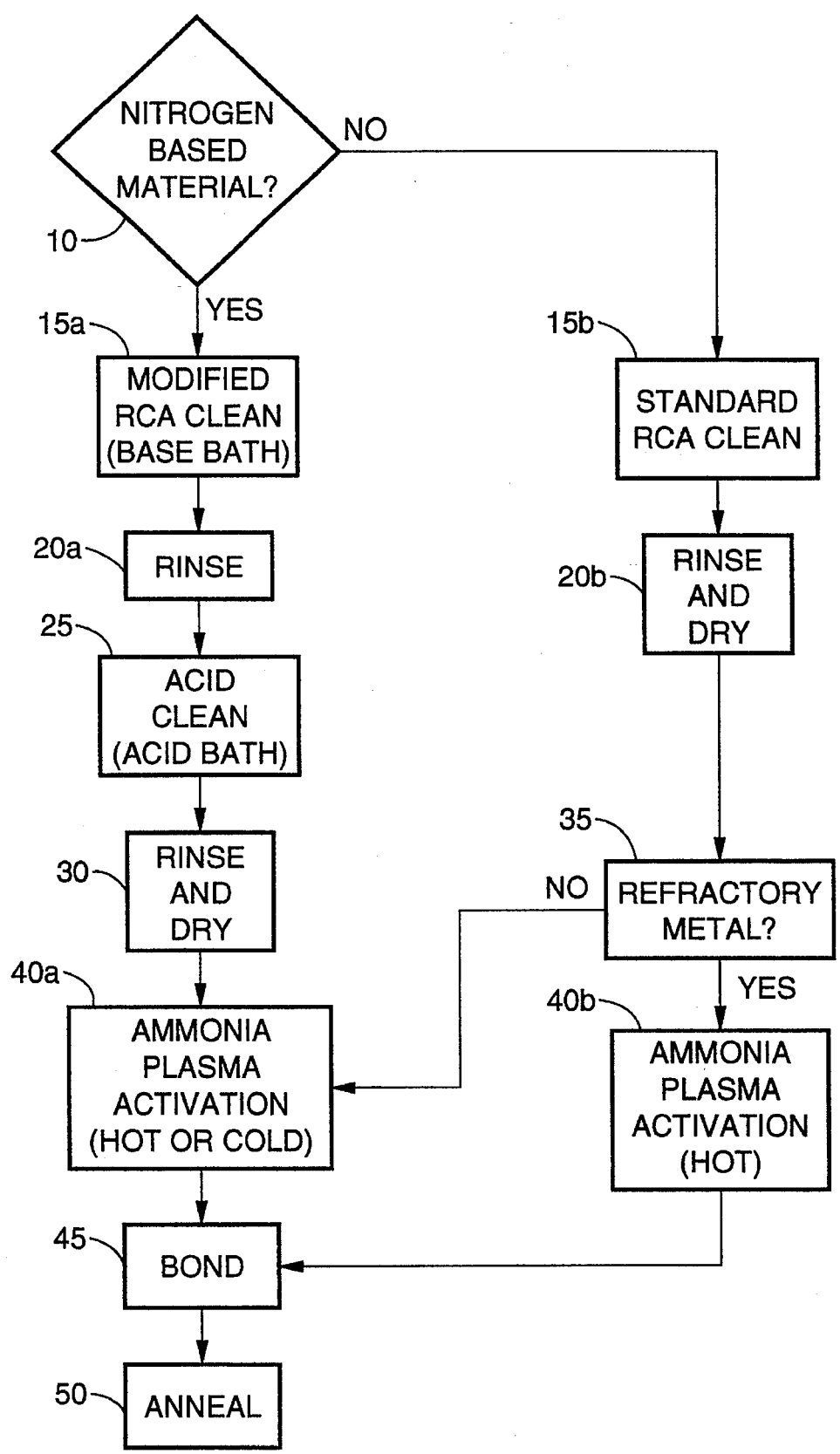
FIG. 1 is a flow chart of the process of the present invention showing steps employed for ammonia plasma activation of a nitrogen based or non-nitrogen based material.
Figure 2:
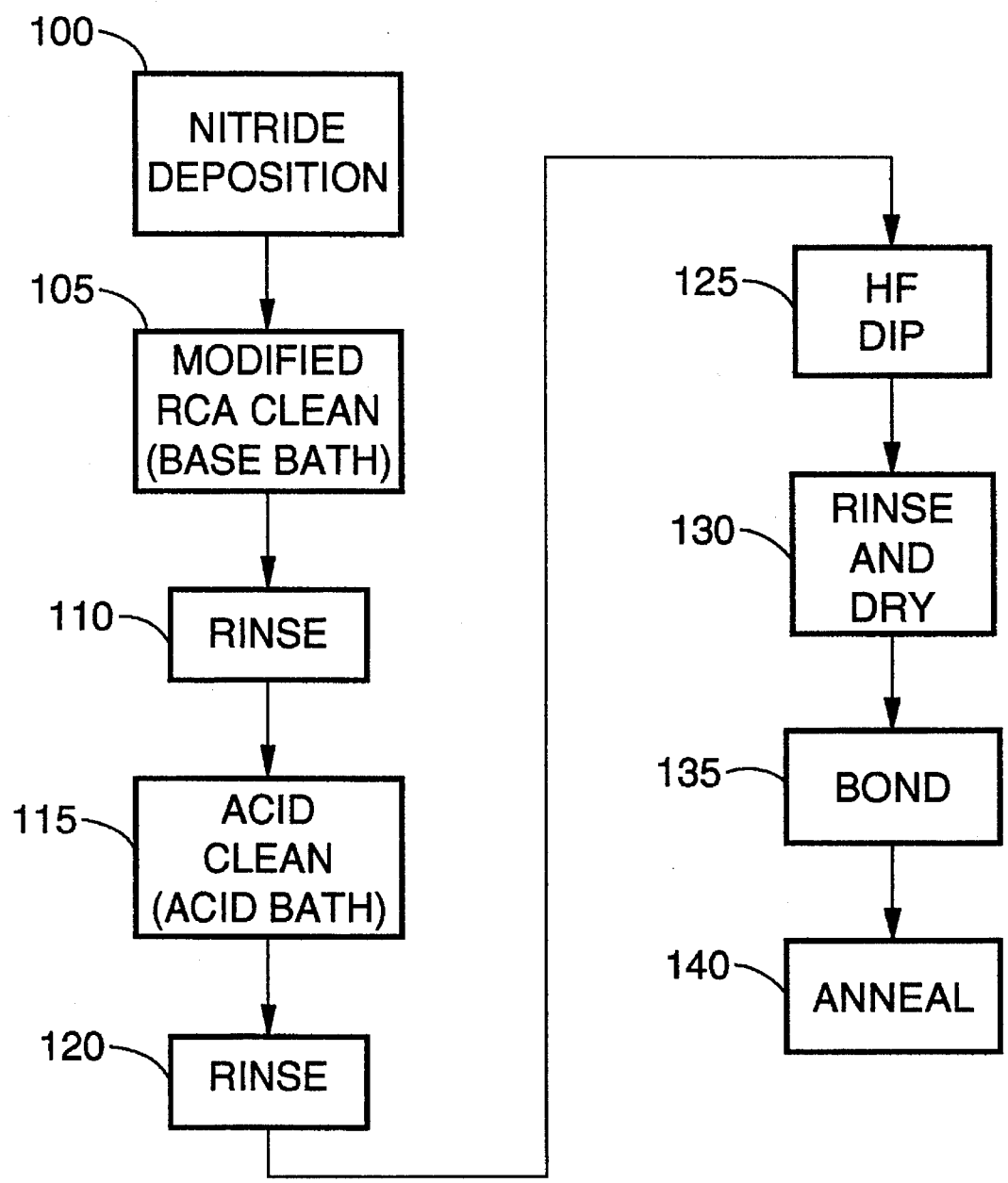
FIG. 2 is a flow chart of an alternative embodiment of the process of the present invention showing steps employed for hydrofluoric acid activation of a nitride surface.

Referring more specifically to the drawings, for illustrative purposes the present invention is embodied in the process steps generally shown in the flow charts of FIG. 1 and FIG. 2. It will be appreciated that the steps and their sequence may vary without departing from the basic concepts as disclosed herein.

We have discovered that, by establishing nitrogen based radicals on the surface of a material to be bonded, the surface will become hydrophilic and reactive for low temperature direct bonding. The surface can then be initially bonded to another hydrophilic and reactive surface at room temperature by bringing the surfaces into physical contact. Strengthening of the bond to render it permanent and useful will then occur at temperatures below approximately 500° C. and typically in the range of approximately 90° C. to approximately 300° C., depending upon the particular material being bonded and the amount of time in the annealing furnace. Increasing the annealing temperature will reduce the time required for annealing stage to be completed.

FIG. 1 shows the preferred embodiment of a generalized bonding process using ammonia plasma activation. At step 10 a determination is made as to whether the surface of the material is nitrogen based or non-nitrogen based. Examples of nitrogen based materials are silicon nitride, titanium nitride, other metal nitrides and the like. Examples of non-nitrogen based materials are titanium, other metals, metal silicides, silicon (including single crystal polysilicon and amorphous silicon), silicon dioxide, and the like. In the case of a nitrogen based material, at step 15a the surface is cleaned in a base bath which is a modified RCA clean. A standard RCA clean is not optimum because it will remove a nitride layer or other nitrogen based constituent. Therefore, we have developed a modified RCA clean which has a reduced level of $NH_4OH$. The preferred solution generally comprises approximately a 20:4:1 solution of $H_2O:H_2O_2:NH_4OH$ made with approximately 3200 milliliters of $H_2O$, approximately 640 milliliters of $H_2O_2$, and approximately 160 milliliters of $NH_4OH$. Note that a standard RCA clean would utilize 640 milliliters of $NH_4OH$. Preferably, the base bath solution is heated to a temperature of approximately 75° C. and the cleaning process is terminated after approximately 10 minutes.

After the material is cleaned with the base bath, it is rinsed at step 20a. Thereafter, the material surface is cleaned with an acid bath at step 25. The preferred solution generally comprises approximately a 6:1:1 solution of $H_2O:H_2O_2:HCL$ made with approximately 3000 milliliters of $H_2O$, approximately 450 milliliters of $H_2O_2$, and approximately 450 milliliters of HCL. Preferably, the acid bath solution is heated to a temperature of approximately 75° C. and the cleaning process is terminated after approximately 10 minutes. The material surface is again rinsed and dried at step 30.

At step 40a, the material undergoes ammonia plasma activation by being subjected to a plasma of $NH_3$ at a temperature between approximately 25° C. and 350° C. for at least 5 minutes. For example, silicon and silicon nitride can be plasma activated at room temperature or any temperature falling within that range. However, as will be discussed herein, hot plasma activation (e.g., 300° C.) would typically be used where the plasma activation occurs as part of, and immediately after, nitride deposition. At the end of this step, the material surface will be both hydrophilic and reactive for low temperature direct bonding.

The material surface is then brought into physical contact with a second hydrophilic and reactive surface at step 45 where an initial bond forms. At step 50 the initially bonded materials are annealed at a temperature which is preferably approximately 300° C. At that temperature, a strong bond will occur in several days (e.g., approximately 4 days). Effective bonding can also be achieved with anneal temperatures between approximately 90° C. (or lower) and approximately 500° C. (or higher), the logarithm of the time for bonding being inversely proportional to an increase in temperature.

It should be noted at this point that ammonia plasma activation, as applied to nitrogen based materials such as silicon nitride, can be employed as a step in the deposition of the nitride layer as well as at some later point in time. For example, a layer of $Si_3N_4$ would typically be grown on a silicon wafer to a thickness of approximately 500 Å using plasma enhanced chemical deposition at 300° C. In doing so, 55 sccm $NH_3$ would be leaked into the deposition chamber along with 20 sccm $SiH_4$. Pressure would typically be set at 700 millitorr and an electromagnetic radiation field established at 13.6 MHz with 26 watts of power. Striking the plasma initiates the deposition which preferably occurs at a rate of 125 Å per minute. Once the desired thickness is reached, the $SiH_4$ is shut down and the plasma reduced to $NH_3$. The $NH_3$ is then shut down, the power is turned off, and the material is removed from the deposition chamber. At this point, the nitride layer is hydrophilic and reactive for low temperature bonding.

In the case of a non-nitrogen based material surface, at step 15b the surface is cleaned in a base bath which is a standard RCA clean. The material surface is then rinsed and dried at step 20b. At step 35 a determination is made as to whether the material to be bonded is a refractory metal. If so, at step 40b the ammonia activation employed is preferably by means of plasma enhanced chemical vapor deposition in a deposition chamber at a temperature of approximately 300° C., with approximately 100 W of power, and with an ammonia flow rate of approximately 55 sccm. If the material is not a refractory metal, then the material undergoes ammonia plasma activation (hot or cold) at step 40a. The surface is then bonded at step 45 and annealed at step 50.

Referring to FIG. 2, an alternative embodiment of the process of the present invention can be seen for use with nitride surfaces. This embodiment can include nitride deposition at step 100 or be applied to a pre-existing nitride surface.

At step 105, the material is cleaned in a base bath. Since a standard RCA clean will remove the nitride layer, the modified RCA clean base bath comprising approximately a 20:4:1 solution of $H_2O:H_2O_2:NH_4OH$ as described above is used. Again, the base bath solution is heated to a temperature of approximately 75° C. and the cleaning process is terminated after approximately 10 minutes.

After the material is cleaned with the base bath, it is rinsed at step 110. Thereafter, the material is cleaned with an acid bath at step 115. The preferred solution generally comprises approximately a 6:1:1 solution of $H_2O:H_2O_2:HCL$ as described above, heated to a temperature of approximately 75° C., and employed for approximately 10 minutes. The material is again rinsed at step 120.

At step 125, the material is rendered hydrophilic and reactive for low temperature direct bonding. To do so, the material is dipped in a solution of dilute hydrofluoric acid which is unbuffered. If a buffered solution were used, the standard buffering agent, $NH_4F$, would remove the nitride layer. The solution should contain less than approximately 5% HF, preferably approximately 1% HF, and the material is removed from the solution after approximately 10 seconds. At step 130, the material is again rinsed and dried.

As is the case where plasma activation is used, the material surface is then brought into physical contact with a second hydrophilic and reactive surface at step 135 where an initial bond forms. At step 140 the initially bonded materials are annealed at a temperature preferably of approximately 300° C. At that temperature, a strong bond will occur in several days (e.g., approximately 4 days). Again, effective bonding can also be achieved with anneal temperatures between approximately 90° C. (or lower) and approximately 500° C. (or higher), the logarithm of the time for bonding being inversely proportional to an increase in temperature.

Figure 3:
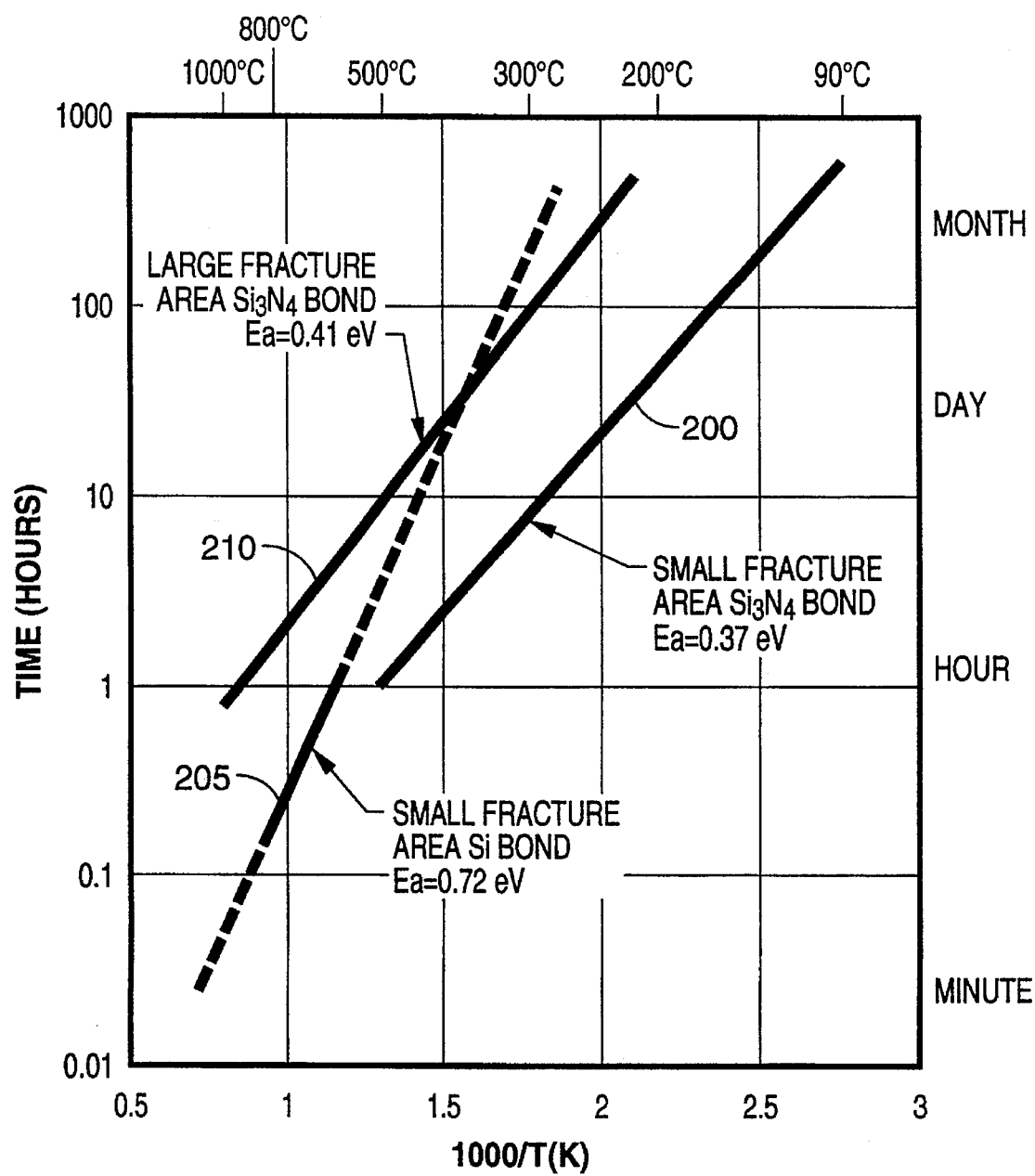
FIG. 3 is a diagrammatic chart showing the time and temperature required to establish comparative strength silicon and silicon nitride bonds during the annealing steps of the processes shown in FIG. 1 and FIG. 2.
Figure 4:
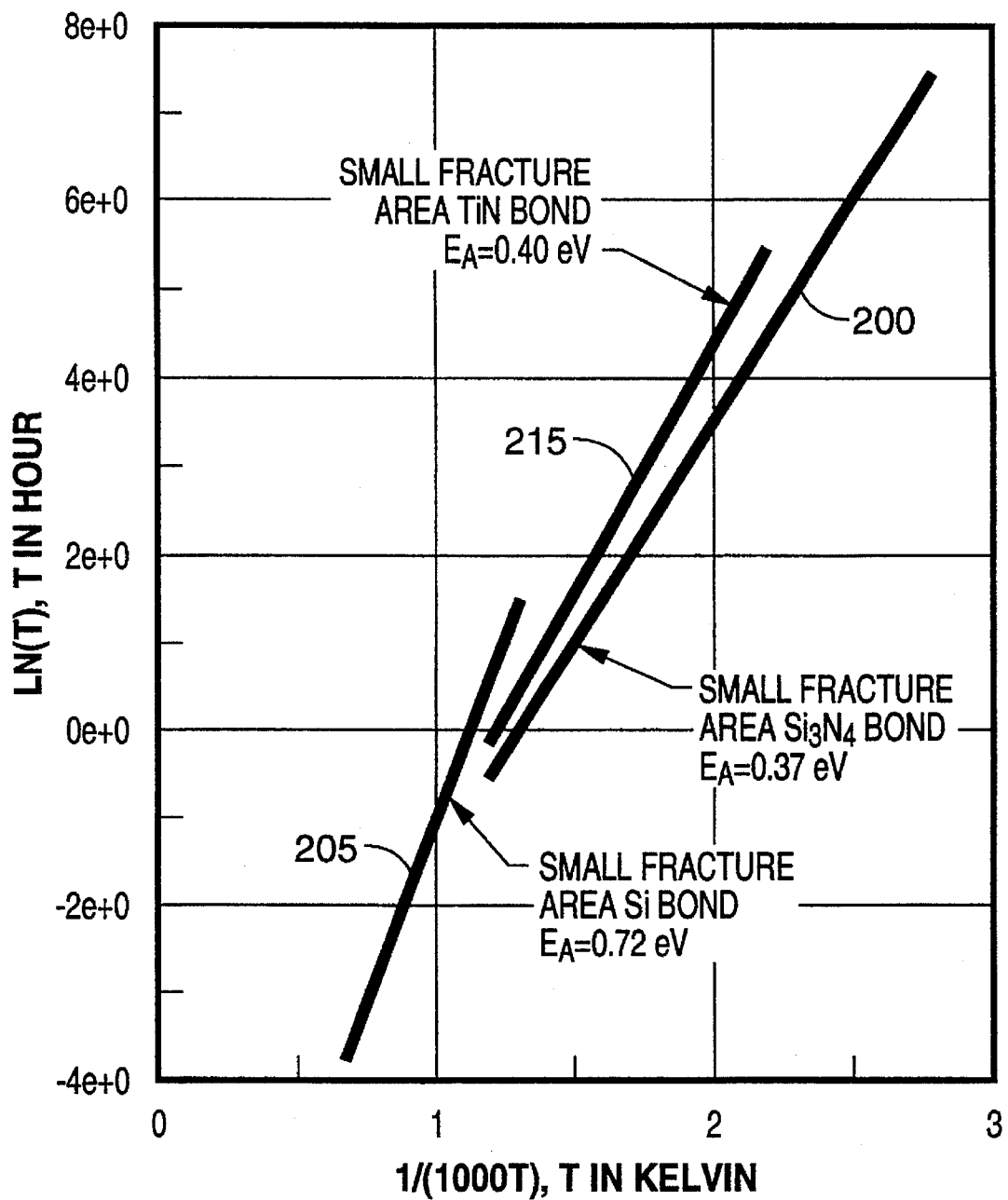
FIG. 4 is a diagrammatic chart showing the time and temperature required to establish comparative strength silicon, silicon nitride, and titanium nitride bonds during the annealing steps of the processes shown in FIG. 1 and FIG. 2.

Referring now to FIG. 3, the rate of growth of the bonded surface is not as rapid as in silicon direct bonding. Various data is shown in FIG. 3 which plots Log(t) versus 1/T, where t is annealing time and T is temperature in Kelvin. This figure plots data for low temperature $Si_3N_4$ bonds as well as for high temperature silicon bonds using the relationship $\ln(t)=Ea/K(1/T)+C$, where C is a constant. For small area fractures, the activation energy, Ea, was found to be approximately 0.37 eV for $Si_3N_4$ direct bonds 200 compared to approximately 0.73 eV for Si direct bonds 205 where the time, t, represents the onset of three dimensional fracture for a tensile pull resulting in fracture of the bonded couple. For large area fractures, Ea is approximately 0.41 eV for $Si_3N_4$ direct bonds 210. Fracture occurs at approximately 2 Mpascals for $Si_3N_4$ direct bonds compared to bulk silicon fracture of approximately 10 Mpascals, the difference being attributable to defects in the substrate caused by the deposited $Si_3N_4$ film. FIG. 4 shows a similar relationship but includes TiN. Here, Ln(t) versus 1/T, where t is annealing time and T is temperature in Kelvin is plotted. For small area fractures, the activation energy for TiN direct bonds 215 is approximately 0.40 eV. This activation energy, which is nearly the same as for for the $Si_3N_4$ direct bonds 200, indicates that the activation mechanisms and surface chemistry is essentially the same for both materials.

Material preparation for low temperature nitrogen bonding is similar to that required for bonding of other thin film deposited materials. Surface flatness and roughness are important considerations for successfully bonding the materials. Preferably in the case of a 500 micrometer thick silicon wafer the radius of wafer curvature should be greater than 60 meters, surface microroughness should be less than 10 Å, and waviness (amplitude/spatial wavelength) should be less than approximately $2\times10^{-5}$. For other materials, these values are a function of stiffness (Young's modulus) and thickness.

Accordingly, it will be seen that this invention permits materials to be bonded at low temperatures using nitrogen radicals as a bonding agent. Furthermore, heretofore it has not been thought possible to render nitrides hydrophilic. As a result of this invention, however, materials can be bonded a temperatures far below the temperatures required in conventional direct bonding processes.

As can be seen therefore, the present invention can be employed to bond substrate wafers, as well as complex devices having only certain surface features to be bonded. The process is easily implemented and well suited to a variety of applications requiring low temperature bonding of materials.

Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. A method for direct bonding nitrogen based materials at low temperatures, comprising the steps of:
   (a) creating nitrogen-based radicals on the surface of a material to be bonded, said surface being rendered hydrophilic by the creating of said nitrogen-based radicals, said step of creating nitrogen-based radicals comprising the steps of placing the surface of a nitrogen based material in a solution of dilute unbuffered hydrofluoric acid, said solution including less than approximately five percent HF, whereby said surface is rendered hydrophilic and reactive;
   (b) removing said surface from said solution of dilute hydrofluoric acid after approximately ten seconds;
   (c) bringing said surface into physical contact with a second hydrophilic and reactive surface to form an initial bond at room temperature; and
   annealing said initially bonded surfaces at a temperature below approximately 500° C.

2. A method as recited in claim 1, said step of placing said nitrogen based surface in a solution of dilute unbuffered hydrofluoric acid is preceded by the step of cleaning said surface in a base bath solution at a temperature of approximately 75 ° C. for approximately 10 minutes, said base bath solution comprising approximately a 20:4:1 solution of $H_2O:H_2O_2:NH_4OH$.

3. A method as recited in claim 2, wherein said step of cleaning said surface in said base bath solution is followed by the step of cleaning said surface in an acid bath solution at a temperature of approximately 75 degrees centigrade for approximately minutes, said acid bath solution comprising approximately a 6:1:1 solution of $H_2O:H_2O_2:HCL$.

4. A method for nitrogen based low temperature direct bonding, comprising the steps of:
   (a) creating nitrogen-based radicals on the surface of a material to be bonded by placing said surface in a solution of dilute unbuffered hydrofluoric acid, said solution including less than approximately five percent HF, and thereby rendering said surface rendered hydrophilic and reactive by the creating of said nitrogen-based radicals, said surface including a nitrogen based material;
   (b) bringing said surface into physical contact with a second said hydrophilic and reactive surface to form an initial bond at room temperature; and
   (c) annealing said initially bonded surfaces at a temperature of less than approximately 500° C.

5. A method as recited in claim 4, wherein said solution of dilute unbuffered hydrofluoric acid includes approximately one percent HF.

6. A method as recited in claim 5, wherein said surface is removed from said solution of dilute unbuffered hydrofluoric acid after approximately ten seconds.

7. A method as recited in claim 4, wherein said step of rendering said surface hydrophilic and reactive by creating nitrogen based radicals on said surface is preceded by the step of cleaning said surface in a base bath comprising approximately a 20:4:1 solution of $H_2O:H_2O_2:NH_4OH$.

8. A method as recited in claim 7, further comprising the step of heating said base bath solution to a temperature of approximately 75 degrees centigrade.

9. A method as recited in claim 8, wherein said surface is cleaned in said base bath solution for approximately ten minutes.

10. A method as recited in claim 7, wherein said step of cleaning said surface in a base bath solution is followed by the step of cleaning said surface in an acid bath solution.

11. A method as recited in claim 10, wherein said acid bath solution comprises approximately a 6:1:1 solution of $H_2O:H_2O_2:HCL$.

12. A method as recited in claim 11, further comprising the step of heating said acid bath solution to a temperature of approximately 75 degrees centigrade.

13. A method as recited in claim 12, wherein said surface is cleaned in said acid bath solution for approximately ten minutes.

* * * * *